United States Patent [19]

Perrotta et al.

[11] Patent Number: 5,472,734
[45] Date of Patent: Dec. 5, 1995

[54] APATITE COATING ON ALUMINUM SHEET AND METHOD OF MANUFACTURE

[75] Inventors: Anthony J. Perrotta, Monroeville; Randall B. Minnick, Lower Burrell, both of Pa.

[73] Assignee: Aluminum Company of America, Pittsburgh, Pa.

[21] Appl. No.: 128,860

[22] Filed: Sep. 29, 1993

[51] Int. Cl.$^6$ ........................................... B05D 1/38
[52] U.S. Cl. ................ 427/2; 427/343; 427/327; 427/419.1; 148/253; 428/34.1; 428/469; 428/689; 428/699
[58] Field of Search ................ 427/2.1, 327, 343, 427/419.1; 148/253; 428/34.1, 469, 472.3, 689, 697, 699

[56] References Cited

U.S. PATENT DOCUMENTS

| | | | |
|---|---|---|---|
| 2,685,541 | 8/1954 | Woodburn, Jr. et al. | 427/343 |
| 4,326,305 | 4/1982 | Davidas | 3/1.9 |
| 4,880,610 | 11/1989 | Constantz | 423/305 |
| 4,882,196 | 11/1989 | Shimamune et al. | 427/419.1 |
| 4,897,370 | 1/1990 | Horiguchi et al. | 501/5 |
| 4,911,953 | 3/1990 | Hosonuma et al. | 427/343 |
| 4,960,646 | 10/1990 | Shimamune et al. | 427/419.1 |
| 5,030,474 | 7/1991 | Satta et al. | 427/2 |
| 5,039,546 | 8/1991 | Chung et al. | 427/2 |
| 5,128,169 | 7/1992 | Satta et al. | 427/2 |

*Primary Examiner*—Michael Lusignan
*Assistant Examiner*—Brian K. Talbot
*Attorney, Agent, or Firm*—Glenn E. Klepac

[57] ABSTRACT

A biocompatible coating is formed on an aluminum sheet surface by reacting a surface portion with an aqueous solution containing calcium hydroxide and a more soluble calcium salt to form a hydrocalumite first coating. The first coating is then reacted with a water-soluble phosphate to form a biocompatible coating comprising hydroxyapatite. The hydroxyapatite coating may be reacted with a water-soluble fluoride or fluorophosphate to form a fluorapatite coating.

16 Claims, 2 Drawing Sheets

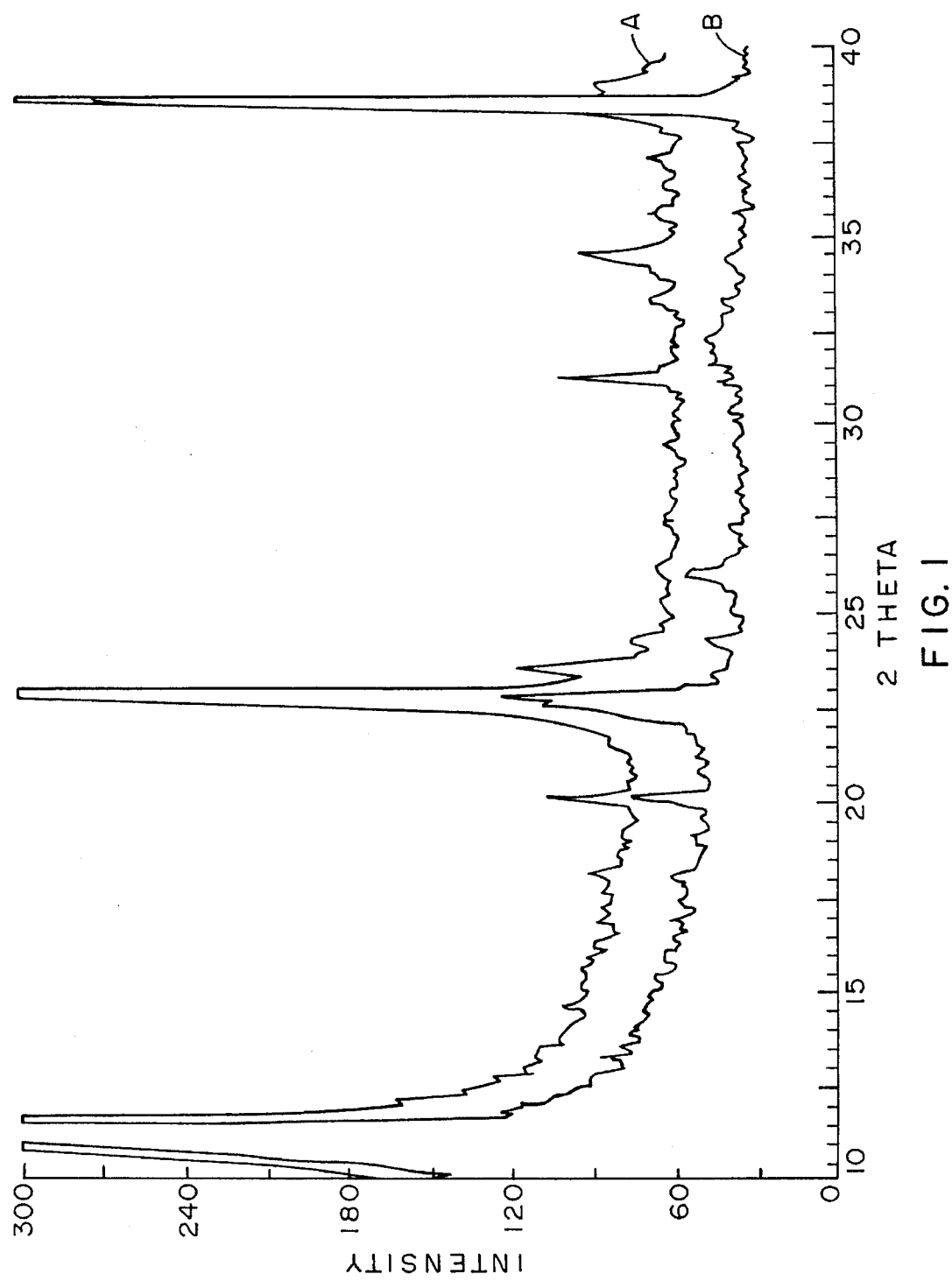

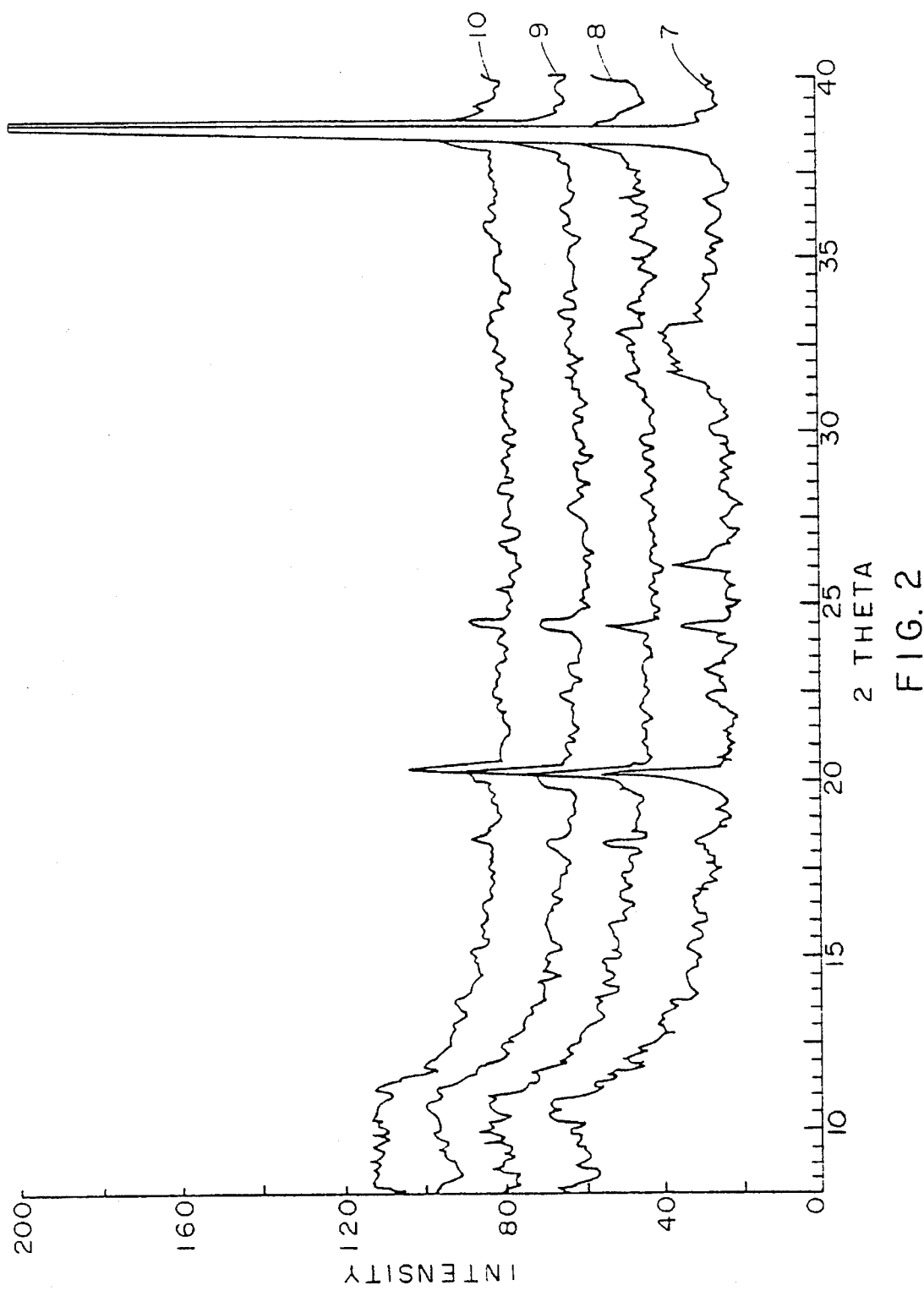

APATITE COATING ON ALUMINUM SHEET AND METHOD OF MANUFACTURE

FIELD OF THE INVENTION

The present invention relates to coatings and films on aluminum sheet and to methods of forming such coatings and films. More particularly, the invention is directed to formation on the sheet of a biocompatible coating consisting principally of apatite.

BACKGROUND OF THE INVENTION

Food and beverage cans are commonly fabricated from aluminum sheet material which is made from aluminum-magnesium alloys such as 5042 and 5182 (AA series) that are heat tempered. The aluminum alloy sheet is normally conversion coated with a solution containing chromium and phosphate before being coated with a polymer such as polyvinylchloride. Because of environmental concerns, there is a need to replace the chromium in this conversion coating.

Apatite is a form of calcium phosphate occurring naturally in the earth's crust. It is a biocompatible mineral that is the main constituent of human teeth and bones. Accordingly, apatite is considered a viable alternative to presently-used chromium phosphate conversion coatings.

It is a principal objective of the present invention to provide a biocompatible coating suitable for use on aluminum sheet.

A related objective of the invention is to form an adhering coating of biocompatible apatite on aluminum sheet using interfacial reactions.

A further objective of the invention is to provide a rapid, commercially useful process for forming the apatite coating on aluminum sheet.

BRIEF DESCRIPTION OF THE DRAWINGS

FIGS. 1 and 2 are x-ray diffraction patterns of coatings made in accordance with the present invention.

SUMMARY OF THE INVENTION

In accordance with the present invention, there is provided a process for coating an aluminum or aluminum alloy substrate it situ with apatite. A particularly preferred substrate comprises an aluminum-magnesium alloy and has a generally planar surface portion.

The surface portion is preferably first reacted with an aqueous solution containing calcium hydroxide and a calcium salt having greater solubility in water than calcium hydroxide. Some suitable calcium salts are calcium chloride, calcium nitrate and calcium acetate. The first aqueous solution has a temperature of about 0°–100° C. and a pH of about 9–12. The result of this initial reaction is a first coating comprising hydrocalumite. A particularly preferred hydrocalumite has the chemical formula $CaAl(OH)_6(Cl,OH)$.

The hydrocalumite coating is reacted with a phosphate dissolved in a second aqueous solution having a temperature of about 60°–100° C. Examples of suitable phosphates are sodium phosphate, ammonium phosphate and potassium phosphate. As a result of treatment with the phosphate, the hydrocalumite coating is transformed into a second coating comprising hydroxyapatite.

In a third step of the claimed process, the second coating is reacted with an aqueous solution containing a water-soluble fluoride or fluorophosphate, thereby forming a third coating comprising fluorapatite. Some suitable fluorine-containing reactants are sodium fluorophosphate, potassium fluorophosphate and ammonium fluorophosphate.

The invention may also be useful for producing an apatite coating on metals other than aluminum, for example, copper or steel. A surface portion of the metal is first plated with aluminum to form a surface portion comprising aluminum. The aluminum is reacted with calcium hydroxide and a water-soluble calcium salt in a first aqueous solution, thereby forming a first coating comprising hydrocalumite. The hydrocalumite first coating is reacted with a water-soluble phosphate to form a second coating comprising hydroxyapatite on the substrate.

In an alternative embodiment of the invention, a water-soluble inorganic phosphate is reacted with the sheet surface to form a first coating comprising aluminum phosphate. The first coating is then reacted with an aqueous solution containing calcium hydroxide and a calcium salt having greater solubility in water than calcium hydroxide to form a second coating comprising hydroxyapatite. The more soluble calcium salt may be calcium chloride, calcium nitrate or calcium acetate.

DETAILED DESCRIPTION OF A PREFERRED EMBODIMENT

One aspect of the present invention is directed toward coating an aluminum alloy sheet substrate with a surface coating comprising a single layer or multiple layers of apatite deposited on a desired surface portion of the substrate from an aqueous solution. The coating has a nontoxic composition and is compatible with deposition of various polymers, such as polyvinyl chloride, thereby ensuring that the aluminum sheet is not attacked by food or drink held in a container made from the coated sheet. The coated sheet material is formed into a can body or end wall.

In depositing the coating on an aluminum sheet, an important first step is to insure that the aluminum substrate is sufficiently clean to promote growth of the apatite coating and good adhesion to the substrate. Conventional chemical coating means for aluminum sheet surfaces allow good results to be obtained.

In a preferred embodiment, a hydrocalumite coating is formed on the cleaned substrate surface by reacting a surface portion with calcium ions in an aqueous calcium chloride solution, with simultaneous activation of the sheet surface. Aluminum ions produced by oxidative dissolution of the aluminum sheet surface combine with calcium ions to form hydrocalumite, $CaAl(OH)_6(Cl,OH)$, in the first step. The second step involves conversion of the hydrocalumite coating on the sheet surface to an apatite coating by a second interfacial reaction with a phosphate solution. Various parameters include concentrations of the reactants, pH, temperature and time for reaction (residence time) are controlled to achieve the desired coating with an appropriate deposition rate.

EXAMPLE 1

A 5042 (AA series) aluminum-magnesium alloy sheet was cleaned and then dipped into an aqueous solution for 60 minutes at room temperature. The solution was formed by mixing 100 ml of a solution containing 0.5 g/L $Ca(OH)_2$ with 4 ml of a solution containing 500 g/L $CaCl_2 \cdot 2H_2O$. The final pH of this first solution was 11.6 The hydrocalumite surface coating thereby formed was then reacted with a solution containing 0.6 moles (34.5 g) $H_3PO_4$ in 500 ml $H_2O$ which was adjusted to a pH of 11 with sodium hydroxide. The reaction was carried out at a temperature of 50° C. for 10 minutes. The x-ray diffraction pattern reveals peaks for hydrocalumite and aluminum, and apatite peaks at 26° and 32°.

EXAMPLES 2–6

The 5042 aluminum alloy sheet was dipped into the $Ca(OH)_2$ and $CaCl_2$ solution described above for 10 minutes at room temperature to form a hydrocalumite coating. The x-ray diffraction pattern of this coating (A in FIG. 1) reveals peaks for hydrocalumite at 11° and 23° and for aluminum at 38°. The hydrocalumite-coated sheet was then reacted with the following solutions:

| Example | Solute | pH | Temperature (°C.) | Time (min.) |
|---|---|---|---|---|
| 2 | Sodium phosphate | 10 | 95 | 4.5 |
| 3 | Ammonium phosphate | 7 | 85 | 4.5 |
| 4 | Sodium phosphate | 7 | 85 | 4.5 |
| 5 | Ammonium fluorophosphate | 6 | 85 | 4.5 |
| 6 | Sodium fluorophosphate | 6 | 85 | 4.5 |

The x-ray diffraction pattern for the coating of Example 2 is shown in FIG. 1 (curve B). This pattern reveals peaks for apatite at 26° and 32°, along with peaks of reduced intensity for hydrocalumite at 11° and 23°.

EXAMPLES 7–10

In the following examples, the substrate was treated with $Ca(OH)_2$-$CaCl_2$ solution for varying times to form a hydrocalumite first coating. The hydrocalumite coating was then treated with sodium phosphate solution at pH 10 and 95° C. for varying times to form a hydroxyapatite coating. Finally, the hydroxyapatite coating was passivated by treatment with sodium fluorophosphate, $Na_2PO_3F$, at pH 6 and 95° C. for varying times.

| Example | $Ca(OH)_2$—$CaCl_2$ Treatment Time | $Na_3PO_4$ Treatment Time | $Na_2PO_3F$ Treatment Time |
|---|---|---|---|
| 7 | 2 min. | 2 min. | 6 sec. |
| 8 | 1 min. | 1 min. | 7 sec. |
| 9 | 15 sec. | 1 min. | 5 sec. |
| 10 | 15 sec. | 30 sec. | 8 sec. |

FIG. 2 shows the x-ray diffraction patterns of coatings formed in Examples 7–10. The apatite peaks are most pronounced in Example 7.

The coatings of Examples 7–10 were also analyzed for chemical composition by ESCA (Electron Spectroscopy Chemical Analysis). The ESCA results in the table below reveal greater than 20 atomic percent fluorine concentrations in all four coatings analyzed.

| Example | C | O | F | Na | Mg | Al | P | S | Ca |
|---|---|---|---|---|---|---|---|---|---|
| 7 | 9.4 | 36.7 | 20.6 | 6.3 | 3.8 | 5.8 | 6.9 | 0.7 | 9.9 |
| 8 | 13.4 | 19.9 | 36.1 | 10.3 | 4.9 | 6.3 | 3.2 | 0.4 | 5.4 |
| 9 | 15.6 | 19.3 | 35.7 | 11.2 | 3.8 | 7.2 | 2.6 | 0.6 | 4.0 |
| 10 | 14.0 | 15.7 | 40.1 | 12.3 | 4.2 | 7.3 | 1.8 | 0.3 | 4.2 |

Apatite coatings made in accordance with the invention have also been analyzed by Fourier Transform Infrared (FTIR) spectroscopy. Results show that FTIR spectroscopy is extremely sensitive to changes in the crystalline amorphous apatite structure. FTIR is capable of detecting the more amorphous material, as opposed to conventional x-ray analysis which cannot detect it except when it is highly crystallized.

The foregoing description of our invention has been made with reference to a particularly preferred embodiment. Persons skilled in the art will understand that numerous changes and modifications may be made therein without departing from the spirit and scope of the following claims.

What is claimed is:

1. A process for coating an aluminum or aluminum alloy substrate comprising:

(a) providing an aluminum or aluminum alloy substrate having a surface portion:

(b) reacting aluminum in said surface portion with a hydrocalumite aqueous solution containing calcium hydroxide and a calcium salt having greater solubility in water than calcium hydroxide, thereby to form a first coating on the substrate; and (c) reacting said hydrocalumite coating with a water-soluble phosphate to form a hydroxyapatite coating.

2. The process in accordance with claim 1 wherein said surface portion is generally planar.

3. The process in accordance with claim 1 wherein said first aqueous solution has a temperature of about 0°–100° C.

4. The process in accordance with claim 1 wherein said first aqueous solution has a pH of about 9–12.

5. The process in accordance with claim 1 wherein said calcium salt is selected from the group consisting of calcium chloride, calcium nitrate and calcium acetate.

6. The process in accordance with claim 1 wherein step (c) comprises reacting said first coating with a phosphate dissolved in a second aqueous solution having a temperature of about 60°–100° C.

7. The process in accordance with claim 1 wherein said phosphate is selected from the group consisting of sodium phosphate, ammonium phosphate and potassium phosphate.

8. The process in accordance with claim 1 wherein said first aqueous solution has a pH of about 11.6.

9. The process in accordance with claim 1 further comprising:

(d) reacting said hydroxyapatite coating with a water-soluble fluoride or fluorophosphate, thereby to transform said second coating into a third coating comprising fluorapatite.

10. The process in accordance with claim 9 wherein step (d) comprises contacting said hydroxyapatite coating with a third aqueous solution containing sodium fluorophosphate or potassium fluorophosphate.

11. A process for coating an aluminum or aluminum alloy substrate comprising:

(a) providing an aluminum or aluminum alloy substrate having a surface portion;

(b) reacting aluminum in said surface portion with a water-soluble inorganic phosphate, thereby to form a first coating comprising aluminum phosphate on said substrate; and (c) reacting said first coating with calcium hydroxide and a calcium salt having greater solubility in water than calcium hydroxide, thereby to form a second coating comprising hydroxyapatite.

12. The process in accordance with claim 11 wherein said calcium hydroxide and said calcium salt in step (c) are dissolved in an aqueous solution having a pH of about 9–12.

13. The process in accordance with claim 12 wherein said aqueous solution has a pH of about 11.6.

14. A process for coating a metal substrate comprising:
   (a) providing a metal substrate having a surface portion comprising aluminum;
   (b) reacting the aluminum in said surface portion with a first aqueous solution containing calcium hydroxide and a calcium salt having greater solubility in water than calcium hydroxide, thereby to form a first coating comprising hydrocalumite on the substrate; and
   (c) reacting said hydrocalumite in the first coating with a water-soluble phosphate, thereby to form a second coating comprising hydroxyapatite on the substrate.

15. The process in accordance with claim 14 wherein said first aqueous solution has a pH of about 9–12.

16. The process in accordance with claim 14 wherein said first aqueous solution has a pH of about 11.6.

* * * * *